United States Patent [19]

Economides et al.

[11] Patent Number: 4,811,738
[45] Date of Patent: Mar. 14, 1989

[54] CARDIAC PACEMAKER CIRCUIT WITH FAST STORED CHARGE REDUCTION

[75] Inventors: Apollo P. Economides; Stephen Gergely; Christopher Walton, all of Coventry, England

[73] Assignee: Coventry City Council, Coventry, Great Britain

[21] Appl. No.: 53,135

[22] Filed: May 21, 1987

[30] Foreign Application Priority Data

May 23, 1986 [GB] United Kingdom ............... 8612659

[51] Int. Cl.$^4$ .............................................. A61N 1/36
[52] U.S. Cl. ............................................ 128/419 PG
[58] Field of Search .................... 128/419 PG

[56] References Cited

U.S. PATENT DOCUMENTS

| | | | |
|---|---|---|---|
| 3,835,865 | 9/1974 | Bowers | 128/419 PG |
| 4,170,999 | 10/1979 | Allen et al. | 128/419 PG |
| 4,343,312 | 8/1982 | Cals | 128/419 PG |

Primary Examiner—William E. Kamm
Attorney, Agent, or Firm—Renner, Otto, Boisselle & Sklar

[57] ABSTRACT

A cardiac pacemaker circuit for use with a stimulating electrode embedded in a patient's atrium or ventricle and a reference electrode positioned outside the heart or on the same lead within the heart. Stimulus pulses are applied by the circuit across the two electrodes, these stimulus pulses replacing evoked pulses. On termination of each stimulus pulse the amount of charge stored between the two electrodes is monitored and pulses of short duration are applied to the stimulating electrode progressively to reduce this charge over a very short time period to a level at which the intrinsic pulses of the evoked heart response can be monitored. The evoked heart response can then be used for diagnosis while the pacemaker circuit is in operation. If the stored charge was not reduced quickly then the charge would mask the intrinsic pulse and the pacemaker would have to be switched off before the intrinsic pulses could be monitored for diagnosis.

7 Claims, 4 Drawing Sheets

CARDIAC PACEMAKER CIRCUIT WITH FAST STORED CHARGE REDUCTION

This invention relates to a cardiac pacemaker circuit.

BACKGROUND OF THE INVENTION

Intrinsic cardiac pulses may be measured using an electrode placed in or in the vicinity of a heart and an example of such pulses for a healthy patient is shown in FIG. 1A. For each heartbeat, the pulses comprise a wave labelled P which causes the atria to contract, and a complex wave form labelled QRST associated with the contraction of the ventricles. A pacemaker circuit comprises a pulse generator connected to a stimulating electrode embedded in the patient's atrium or ventricle and a reference electrode positioned outside the heart in a unipolar configuration, or on the same lead within the heart in a bipolar system. The generator applies stimulus pulses across these two electrodes which replaces the evoked pulses. During each stimulus pulse, electrical charge is stored in the interface between the stimulus electrode and the myocardium, and the charge then decays upon termination of the stimulus pulse. An example of the waveform appearing at the stimulus electrode is shown in FIG. 1B in which each stimulus pulse is denoted by St. As may be seen, the charge which is stored and its subsequent decay masks the evoked heart response. However, it is useful to detect these evoked pulses as they may be used both for diagnosis and for modifying the operation of the pacemaker circuit.

SUMMARY OF THE INVENTION

The subject invention provides a new pacemaker circuit in which the masking of the evoked heart pulses by the charge stored between the stimulus electrode and the myocardium is reduced or removed.

According to this invention there is provided a cardiac pacemaker circuit including a terminal for connection to a stimulatings electrode, a terminal for connection to a reference electrode, means for applying a stimulus pulse across said stimulating terminal and said reference terminal in response to a timing signal, means for generating said timing signal, and means connected to said stimulating electrode and said reference electrode which are operable, in use, upon termination of the stimulus pulse to remove charge stored between the stimulating electrode and the reference electrode.

By removing the charge which is stored between the stimulating electrode and the tissue, the masking which is caused by such charge is removed.

Said stimulus pulse applying means may comprise a reference voltage source, a resistor and capacitor connected in series between the voltage reference source and the stimulating terminal, and a switch responsive to the timing signal connected between the junction of the resistor and capacitor and the reference terminal.

The charge removing means may be connected to the junction of the resistor and capacitor.

In a preferred embodiment of this invention, said charge removing means is arranged to sample the voltage difference between the stimulating terminal and the reference terminal upon termination of a stimulus pulse and to apply an electrical pulse across the electrodes in accordance with the result of the sampling operation. The charge removing means may be arranged to form a plurality of sampling operations upon termination of a stimulus pulse, each sampling operation being followed by the application of an electrical pulse.

In an alternative arrangement of this invention, the charge removing means is arranged to measure the quantity of charge supplied to a stimulus pulse and to remove substantially an identical quantity of charge upon termination of the stimulus pulse.

The charge removing means may be arranged to clamp the potential difference between the stimulating electrode and the reference electrode for a preset period after removing said substantially identical quantity of charge.

The pacemaker circuit may include a resistor connected in series with one of the stimulating electrode ad the reference electrode, the charge supplied during the stimulus pulse and the charge subsequently removed being measured by integrating the voltage across said resistor with respect to time.

BRIEF DESCRIPTION OF THE DRAWINGS

This invention will now be described in more details with reference to the accompanying drawings in which.

DETAILED DESCRIPTION

Figure 1A:
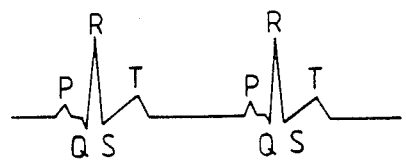
FIGS. 1A and 1B show waveforms of the electrical activity appearing in the heart of a healthy patient and a waveform appearing at the stimulating electrode of a pacemaker circuit.
Figure 1B:
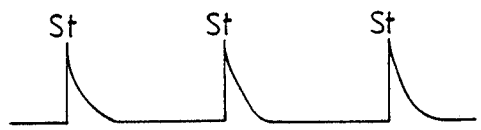
Figure 2:
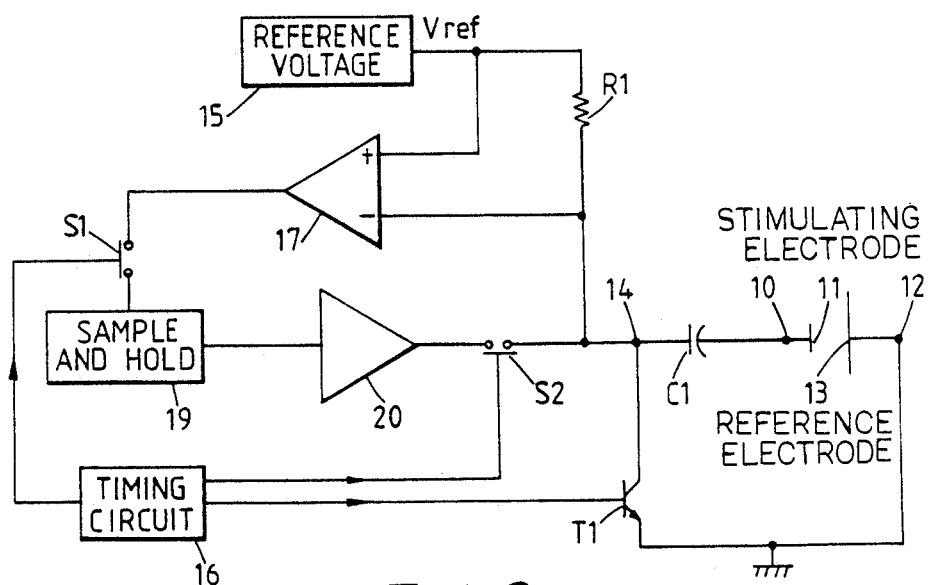
FIG. 2 is a block diagram of a preferred embodiment of this invention.

Referring now to FIG. 2, there is shown a cardiac pacemaker circuit which has a stimulating terminal 10 connected to a stimulating electrode 11 and a reference terminal 12 connected to a reference electrode 13. The reference terminal 12 is connected to the earth line. The stimulating terminal 10 is connected through a capacitor C1 to a terminal 14. The terminal 14 is connected through a resistor R1 to a reference voltage source 15 and also through the collector emitter path of the transistor T1 to the earth line. The base of transistor T1 receives a series of pulses from a timing circuit 16. The components described so far are conventional in pacemaker circuits. In operation, the capacitor C1 is charged by the reference voltage source 15 and, each time a pulse is supplied to the base of transistor T1, a stimulus pulse is supplied across the electrodes 11 and 13. Each stimulus pulse is variable both in amplitude and duration.

The reference voltage source 15 and terminal 14 are connected to the two inputs of an amplifier 17 which subtracts the voltage appearing at terminal 14 from the reference voltage $V_{ref}$, amplifies the result, inverts it and adds to it an offset equal in magnitude to $V_{ref}$. The output of amplifier 17 is connected through an analog switch S1 to a sample and hold circuit 19. The output of circuit 19 is connected to an amplifier 20 and analog switch S2 to terminal 14. The switches S1 and S2 are controlled by the timing circuit 16. In operation, immediately upon termination of each stimulus pulse, switch S1 is closed and switch S2 is opened for a preset period and the output of amplifier 17 is sampled and held in circuit 19. Then, switch S1 is opened and switch S2 is closed for a preset period and a voltage pulse is applied to terminal 14 having a magnitude and polarity which is determined by the output of sample and hold circuit 19. This pulse causes some of the charge which has been stored between electrodes 11 and 13 during the stimulus pulse to be removed. The cycle is then repeated a predetermined number of times thereby returning the voltage at terminal 14 to a value substantially equal to $V_{ref}$. Because there is no appreciable change in the voltage across capacitor C1, the series of operations returns the potential at the stimulating electrode substantially to that of the earth line. The intrinsic pulses may then be observed at terminal 14.

Thus, the intrinsic pulses are not masked by the charge which has been stored between electrodes 11 and 13.

The detailed circuit diagram of the pacemaker circuit shown in FIG. 2 will now be described with reference to FIGS. 3 to 5.

Figure 3:
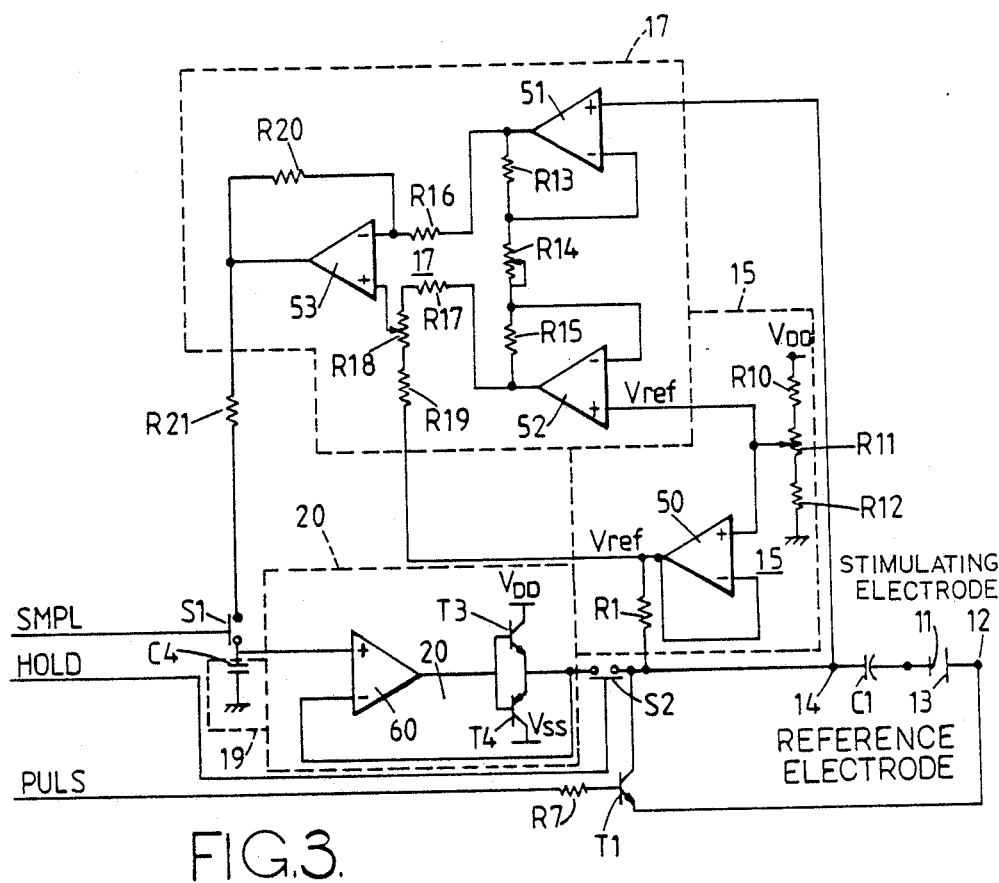
FIGS. 3 and 4 are detailed circuit diagrams of the embodiments shown in FIG. 2.
Figure 4:
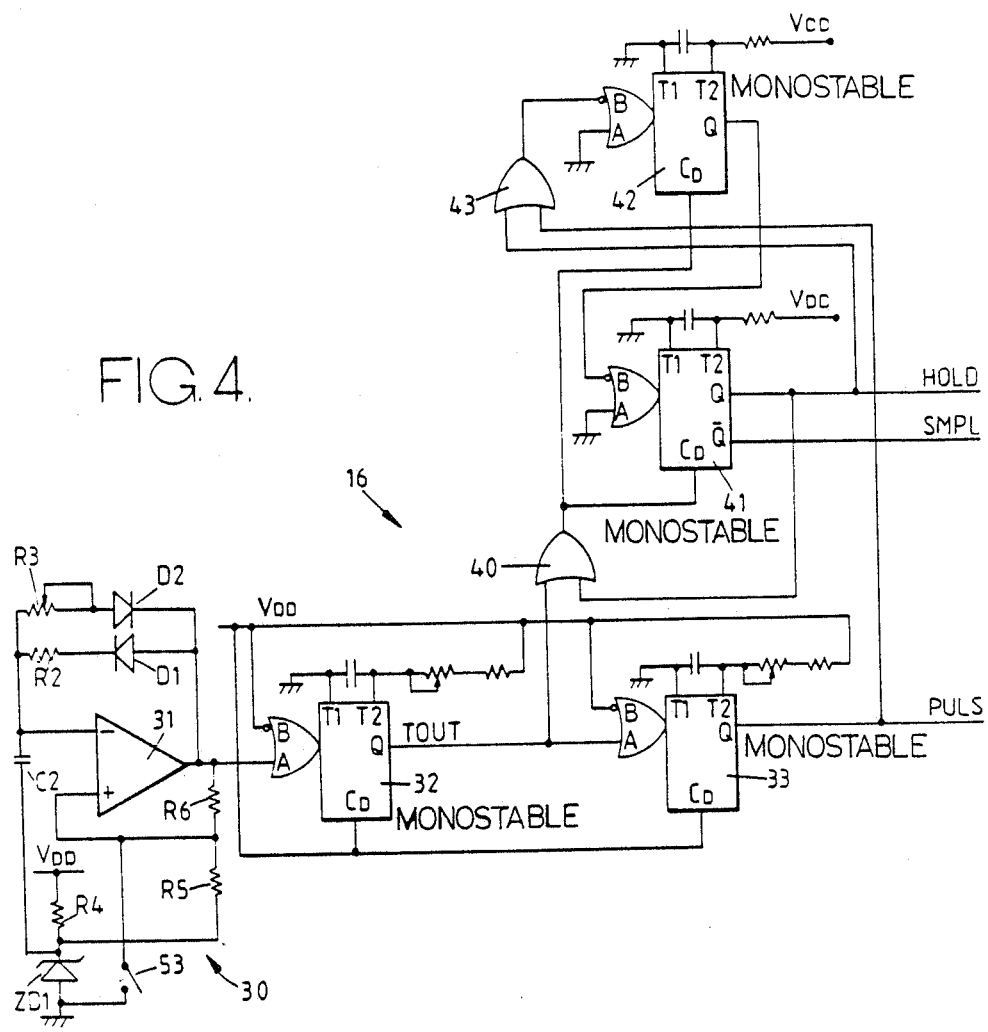
Figure 5:
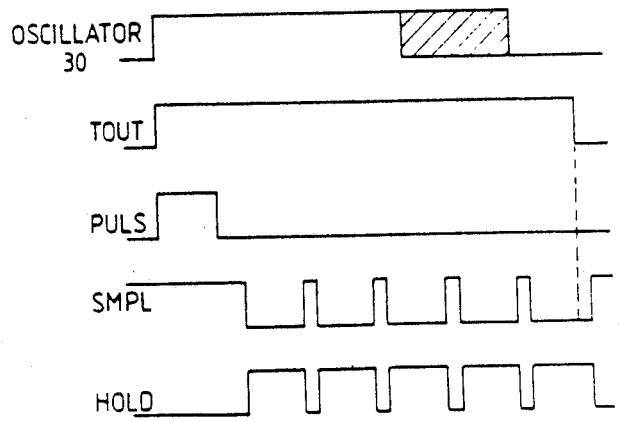
FIG. 5 shows waveforms appearing in the embodiment of FIG. 2.

Referring firstly to FIG. 4, the timing circuit 16 includes an oscillator 30. The oscillator comprises a type 3140 operational amplifier 31, the output of which is connected to its inverting-input through a diode D1 and a resistor R2. The output is also connected to the inverting input through a diode D2 and a preset resistor R3. The inverting input is connected through a capacitor C2 to the junction of a Zener diode ZD1 and a resistor R4 which are connected in series between the positive supply rail and the earth line to provide a bias voltage. This junction is also connected through a resistor R5 and a resistor R6 to the output of amplifier 31 and the junction of these two resistors is connected to the non-inverting input. The non-inverting input is also connected to the earth rail through a switch S3 which may be closed to prevent oscillation. The oscillator 30 provides the basic timing signal of the pacemaker circuit and the resistor R3 may be adjusted to control the frequency of the stimulus pulses. The output of amplifier 31 is connected to the A input of a type 4528 monostable 32 which produces a signal TOUT at its Q output. The Q output of this monostable is connected to the input of a further type 4528 monostable 33 at the Q output of which is produced a signal PULS. As shown in FIG. 3, thesignal PULS is connected to the base of transistor T1 through a resistor R7. The monostable 33 is set to provide pulses having a variable duration.

The Q output of monostable 32 is connected to one input of an OR gate 40, the output of which is connected to the enable inputs $C_D$ of a pair of monostables 41 and 42. The monostable 41 is set to produce pulses having a duration of 0.4 ms and monostable 42 is set to produce pulses having a duration of 25 microseconds. The Q output of monostable 41 is connected to one input of an OR gate 43, the output of which is connected to the B input of monostable 42. The Q output of monostable 42 is connected to the B input of monostable 41. The Q ouput of monostable 41 is also connected to the other input of OR gate 40 and the Q output of monostable 33 is connected to the other input of OR gate 43. The Q output of monostable 41 produces a signal HOLD and is connected to the control terminal of switch S2. The $\overline{Q}$ output of monostable 41 produces a signal SMPL which is connected to the control terminal of switch S1. A waveform diagram is shown in FIG. 5 for the signal appearing at the output of oscillator 30 and for the signals TOUT, PULS, SMPL, and HOLD. As may be observed in FIG. 5, the signal TOUT controls the number of cycles of operation of switches S1 and S2. It may also be observed in FIG. 5 that the switch S1 is always closed immediately upon termination of each stimulation pulse.

Referring more particularly to FIG. 3, the voltage reference source 15 comprises resistor R10, a potentiometer R11 and resistor R12 connected in series between the positive supply rail $V_{DD}$ and the earth line. The tapping on potentiometer R11 provides the reference voltage $V_{ref}$. This junction is connected to the non-inverting input of a type 3140 operational amplifier 50.

The amplifier 17 comprises three type 3140 operational amplifiers 51, 52 and 53 which are connected as an instrumentation amplifier. The non-inverting input of amplifier 51 is connected to terminal 14 and the non-inverting input of amplifier 52 is connected to the tapping on potentiometer R11. The output of amplifier 51 is connected through a resistor R13, a preset resistor R14 and 1 resistor R15 to the output of amplifier 52. The junction of resistors R13 and R14 is connected to the inverting input of amplifier 51 and the junction of resistors R14 and R15 is connected to the inverting input of amplifier 52. The output of amplifier 51 is connected through a resistor R16 to the inverting input of amplifier 53. The output of amplifier 52 is connected through a resistor R17, a potentiometer R18, and a resistor R19 to the output of amplifier 50 and the tapping on potentiometer R18 is connected to the non-inverting input of amplifier 53. The output of amplifier 53 is connected to its inverting input through resistor R20.

The output of amplifier 53 represents the output of amplifier 17 and is connected through a resistor R21 and switch S1 to a capacitor C4 which represents the sample and hold circuit 19. The capacitor C4 is a low leakage polyester type capacitor. It is to be noted that the time constant of resistor R21 in capacitor C4 is 2.5 microseconds which is one tenth of the duration of the pulses of the signal SMPL.

The amplifier 20 is formed from a type 3140 operational amplifier 60 and a pair of transistors T3 and T4 connected between the positive supply line $V_{DD}$ and the negative supply line $V_{ss}$. The emitters of transistors T3 and T4 are commonly connected to the inverting input of amplifier 60 to provide a voltage follower arrangement. The non-inverting input of amplifier 60 is connected to the junction of switch S1 and capacitor C4 and the emitters of transistors T3 and T4 are connected through the switch S2 to terminal 14.

In order to minimise external interference, the lines between the non-inverting input of amplifier 51 and terminal 14 and the non-inverting input of amplifier 52 and the tapping on potentiometer R11 are screened and the entire circuit is enclosed in a die cast box which is earthed. It is also to be noted that the timing circuit 16 is arranged so that there are no logic level transitions during the sampling periods as such transitions could cause internal interference.

Figure 6:
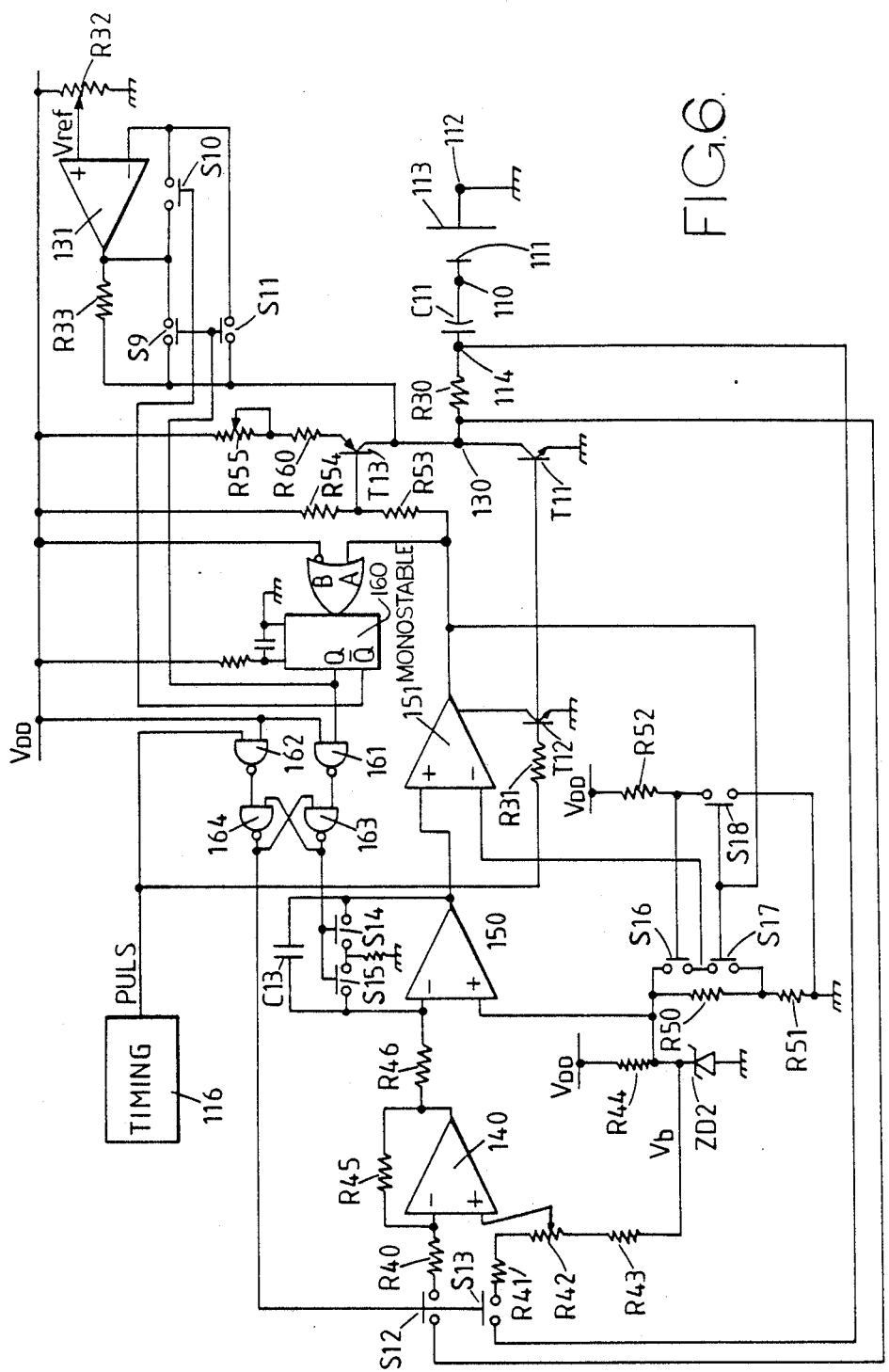
FIG. 6 is a circuit diagram of another embodiment of this invention.

Referring now to FIG. 6, there is shown the circuit diagram of another pacemaker circuit. As will be explained in more detail, in this pacemaker circuit the charge which is stored between the stimulating electrode and the myocardium during each stimulus pulse is measured by using an integrator and a measuring resistor and a substantially equal amount of charge is then removed upon termination of the stimulus pulse.

The circuit shown in FIG. 6 has a stimulating electrode 111 and a reference electrode 113. The electrode 113 is connected to the earth line via a terminal 112. The stimulating electrode 111 is connected via a terminal 110 and a capacitor C11 to a terminal 114. Terminal 114 is connected through a measuring resistor R30 to a terminal 130. The terminal 130 is connected to the earth line through the collector/emitter path of a transistor T11. The pacemaker circuit includes a timing circuit 116 which provides a pulsed signal PULS similar to the signal PULS produced by the circuit shown in FIG. 4. The signal PULS is supplied through a resistor R31 to the base of transistor T11. The pacemaker circuit further includes a potentiometer R32 connected between the positive supply line $V_{DD}$ and the earth line. A tapping on potentiometer R32 provides a reference voltage $V_{ref}$ and this reference signal is supplied to the non-inverting input of a type 3140 operational amplifier 131. The output of amplifier 131 is connected through a resistor R33 to terminal 130. The output of amplifier 131 is also connected through an analog switch S10 to its non-inverting input. Its non-inverting input is also connected through an analog switch S11 to terminal 130 and an analog switch S9 is connected between the output of amplifier 131 and terminal 130. With the exception of switches S9, S10 and S11 and the measuring resistor R30, the components described so far are conventional in a pacemaker circuit. In operation, with the switch S10 closed and switches S9 and S11 open, amplifier 131 charges the capacitor C11 to the voltage $V_{ref}$. Each time a pulse is supplied to the base of transistor T11, the stimulus pulse is applied between electrodes 111 and 113.

Terminal 130 is connected through an analog switch S12 and a resistor R40 to the inverting input of a type 3140 operational amplifier 140. The terminal 114 is connected through an analog switch S13, a resistor R41, a potentiometer R42, and a resistor R43 to the junction of a Zener diode ZD2 and a resistor R44 connected in series between the positive supply line and the earth line. The resistor R44 and Zener diode ZD2 operate to provide a bias voltage $V_b$. A tapping on potentiometer R42 is connected to the non-inverting input of amplifier 140 and its output is connected to its inverting input through a 1 megohm feed back resistor R45. Thus, operational amplifier 140 together with its associated components amplifiers the voltage appearing across the measuring resistor R30.

The output of operational amplifier 140 is connected through a resistor R46 to the inverting input of a type 3140 operational amplifier 150. The non-inverting input of amplifier 150 receives the bias voltage $V_b$. The output of amplifier 150 is connected through an integrating capacitor C13 to its inverting input. The output of amplifier 150 is also connected to its non-inverting input through a pair of analog switches S14 and S15, the junction of switches S14 and S15 being connected through a resistor to the earth line. Thus, amplifier 150 can integrate the current flowing through resistor R30 and so operate as an integrator. When the switches S14 and S15 are closed the integrator is reset.

The output of amplifier 150 is connected to the positive input of a type 311 comparator 151. The junction of resistor R44 and Zener diode ZD2 is connected through a resistor R50 and the resistor R51 to the earth line. Resistor R50 is bridged by a pair of analog switches S16 and S17 and the junction of these switches is connected to the negative input of comparator 151. A resistor R52 and a further analog switch S18 are connected between the positive supply line $V_{DD}$ and the earth line. The junction of resistor R52 and switch S18 is connected to the control terminal of switch S16. The control terminals of switches S17 and S18 are commonly connected together to the output of amplifier 151. Also, the signal PULS is connected through resistor R31 to the base of a transistor T12, the emitter of which is connected to the earth line and the collector of which is connected to the enable input (pin 6) of amplifier 151.

The output of comparator 151 is connected through a resistor R53 and the resistor R54 to the positive supply rail $V_{DD}$ and the junction of these two resistors is connected to the base of a transistor T13. The emitter of transistor T13 is connected through a resistor R54 and a potiometer R55 to the positive supply line $V_{DD}$ and the collector of this transistor is connected to terminal 130. Thus, when transistor T13 is on, this transistor and the associated resistors operate as a current source.

The output of amplifier 151 is connected to the A input of a type 4528 monostable 160. The Q output of this monostable is connected to the control terminal of switch S11 and the $\overline{Q}$ output is connected to the control terminal of switch S10. The Q output of monostable 160 is also connected to one input of a NAND gate 161. NAND gate 161 is associated with another NAND gate 162, one input of which receives the signal PULS. The other input of NAND gates 161 and 162 are connected to the positive supply line $V_{DD}$. The output of NAND gate 161 is connected to one input of a NAND gate 163 and the output of NAND gate 162 is connected to one input of a NAND gate 164. The NAND gates 163 and 164 are connected as a R-S flip flop. The output of NAND gate 163 is connected to the control terminals of switches S13 and S14 and the output of NAND gate 164 is connected to the control terminals of switches S12 and S13.

In operation, immediately before the leading edge of each pulse of the signal PULS, switches S12 and S13 are open, switches S14 and S15 are closed. Consequently, the output of amplifier 150 is clamped to the bias voltage $V_b$. At the leading edge of the pulse of the signal PULS, transistors T11 and T12 are turned on, thereby supplying a stimulus pulse across electrodes 111 and 113 and disabling comparator 151. The leading edge of the pulse also causes the output of NAND gate 164 to go high, thereby closing swithes S12 and S13 and opening switches S14 and S15. Consequently, during the stimulus pulse, the current flowing through resistor R30 is integrated by amplifier 150 and the deviation of the output of this amplifier between the beginning and the end of the pulse represents the charge stored between electrodes 111 and 113. Upon termination of the stimulus pulse, transistors T11 and T12 turn off and comparator 151 is enabled. As the output of amplifier 150 is now below the bias voltage $V_b$, the output of comparator 151 goes low thereby turning on transistor T13 which acts as a current source for removing the charge which has been stored. During charge removal, the current flowing through resistor R30 is again integrated by comparator 150. When the output of comparator 150 reaches the bias voltage $V_b$, the output of comparator 151 goes high thereby turning off transistor T13, triggering monostable 160, closing switches S17 and S18 and opening switch S16. The operation of switches S16 to S18 provides hysteresis for the negative input of comparator 151. As a result of triggering monostable 160, the output of NAND gate 163 goes high and so switches S14 and S15 are closed thereby removing the charge on capacitor C13 and switches S12 and S13 are opened. Whilst the Q output of monostable 160 is high, switches S9 and S11 are closed and switch S10 is open. This has the effect of clamping terminal 130 to the reference voltage $V_{ref}$ thereby substantially removing any remaining charge stored between electrodes 111 and 113. When the Q output of monostable 160 goes low, switches S9 and S11 open and switch S10 closes and the reference voltage $V_{ref}$ is then applied to terminal 130 via a resistor R33.

Therefore, upon termination of each stimulation pulse, the charge stored between electrodes 111 and 113 is substantially removed by transistor T13. In practice, it has been found that the charge is removed at this stage to an accuracy of approximately 0.1%. Because the interface between the stimulus electrode 111 and the myocardium has complex non-linear properties, it is unlikely that this interface will be returned precisely to its initial state and it is for this reason that terminal 130 is then clamped for a preset period to the reference voltage $V_{ref}$. When the terminal 130 is supplied with a reference voltage via resistor R33, the intrinsic pulses in the heart may be sensed at terminal 130.

Thus, in the two embodiments of the invention which have been described, the charge which is stored between the stimulus electrode and the myocardium during the stimulus pulse is subsequently removed thereby making it possible to detect the evoked heart pulses. The evoked pulses may therefore be used for diagnosis whilst the pacemaker circuit is operating. For example, damaged tissue in a heart may cause a secondary wave to follow the due PRST waves and this wave may be detected using the present invention. Also, the pacemaker circuit of the present invention may be modified so that it can detect a specific component of the evoked pulse and use this to modify the operation of the pacemaker circuit. For example, the detection of such a pulse may be used to modify the frequency of intensity of the stimulus pulses or to suppress or trigger them as may be appropriate.

What is claimed is:

1. A cardiac pacemaker circuit comprising:
   a first terminal for connection to a stimulating electrode;
   a second terminal for connection to a reference electrode;
   timing signal means for generating a timing signal;
   stimulating pulse means coupled to said terminals for applying a stimulus pulse across said terminals in response to said timing signal, said stimulus pulse means comprising reference voltage source means for generating a reference voltage and switch means responsive to said timing signal to apply said stimulus pulse from said reference voltage source means to said terminals;
   and charge reducing means operable on termination of said stimulus pulse to reduce charge stored between said terminals for enabling monitoring of intrinsic pulses;
   and wherein said charge reducing means comprises means for repeatedly sampling the voltage difference between said first terminal and said reference voltage means on termination of said stimulus pulse and reducing said stored charge after each said sample until the voltage across said first and second terminals is reduced to a value substantially equal to zero.

2. A pacemaker as claimed in claim 1, wherein said stimulating pulse means includes a series resistance capacitance circuit coupling said reference voltage source means to said first terminal; and wherein said switch means is connected between the junction of said resistance and capacitance and said second terminal.

3. A pacemaker as claimed in claim 1, wherein said charge removing means comprises means for applying a pulse of preselected duration across said first and second terminals of a polarity to reduce the stored charge.

4. A pacemaker circuit as claimed in claim 1, wherein said charge removing means comprises a comparator for comparing said reference voltage with said stimulus terminal voltage and generating an output signal in dependence on said comparison; a sample and hold means for sampling said comparator output signal and applying a signal to said first terminal to reduce said stored charge in dependence on the level of said output signal; and control means for controlling operation of said sample and hold means.

5. A pacemaker as claimed in claim 1, wherein said charge reducing means comprises means for monitoring the quantity of charge supplied to said first terminal by a stimulus pulse and removing substantially an identical quantity of charge on termination of the stimulus pulse.

6. A pacemaker as claimed in claim 5, wherein said charge reducing means comprises means for clamping said first terminal at said reference voltage level for a preset period after removal of said substantially identical quantity of charge.

7. A pacemaker as claimed in claim 5, further comprising a resistance connected in series with one of said terminals and said stimulus pulse means, and means for measuring the charge supplied during said stimulus pulse and the charge removed by integrating the voltage across said resistance with respect to time.

* * * * *